(12) United States Patent
Rashid et al.

(10) Patent No.: US 8,969,416 B2
(45) Date of Patent: Mar. 3, 2015

(54) POLYVINYLPYRROLIDONE-CONTAINING ACETAMINOPHEN LIQUID FORMULATIONS

(75) Inventors: Abdul Rashid, Livingston, NJ (US); Zhang Julia Zhang, Scotch Plains, NJ (US); Minh Tran, Secaucus, NJ (US); Dahai Guo, Belle Mead, NJ (US)

(73) Assignee: Enspire Group LLC, South Plainfield, NJ (US)

( * ) Notice: Subject to any disclaimer, the term of this patent is extended or adjusted under 35 U.S.C. 154(b) by 171 days.

(21) Appl. No.: 13/434,267

(22) Filed: Mar. 29, 2012

(65) Prior Publication Data

US 2013/0261189 A1 Oct. 3, 2013

(51) Int. Cl.
*A61K 31/167* (2006.01)

(52) U.S. Cl.
CPC .................................. *A61K 31/167* (2013.01)
USPC .......................................... 514/630; 424/400

(58) Field of Classification Search
CPC .................................................... A61K 31/167
USPC .......................................... 424/400; 514/630
See application file for complete search history.

(56) References Cited

U.S. PATENT DOCUMENTS

| 5,071,643 | A | 12/1991 | Yu et al. |
| 5,141,961 | A | 8/1992 | Coapman |
| 5,154,926 | A | 10/1992 | Kawasaki et al. |
| 5,409,907 | A | 4/1995 | Blase et al. |
| 5,484,606 | A | 1/1996 | Dhabhar |
| 5,505,961 | A * | 4/1996 | Shelley et al. ................. 424/451 |
| 5,510,389 | A * | 4/1996 | Dhabhar ........................ 514/629 |
| 5,641,512 | A | 6/1997 | Cimiluca |
| 6,160,020 | A | 12/2000 | Ohannesian et al. |
| 6,783,731 | B1 | 8/2004 | Arter et al. |
| 7,029,698 | B2 | 4/2006 | Waranis et al. |
| 2003/0096872 | A1 | 5/2003 | Waranis et al. |
| 2007/0155747 | A1* | 7/2007 | Dasse et al. ................. 514/235.5 |
| 2011/0020440 | A1 | 1/2011 | Modi et al. |

FOREIGN PATENT DOCUMENTS

| WO | 03013481 A1 | 2/2003 |
| WO | 2009066146 A2 | 5/2009 |

OTHER PUBLICATIONS

Folttmann et al., "Drug Delivery Technology", vol. 8 (6), pp. 22-27, Jun. 2008.*

* cited by examiner

*Primary Examiner* — Johann R Richter
*Assistant Examiner* — Yanzhi Zhang
(74) *Attorney, Agent, or Firm* — Fox Rothschild LLP; Jianming Jimmy Hao

(57) ABSTRACT

A pharmaceutical formulation contains 10-60% by weight acetaminophen as the only active ingredient and a solvent system for dissolving the acetaminophen. The formulation is free of any ionizing agent and its solvent system includes water, polyethylene glycol, and polyvinylpyrrolidone that is 2-50% by weight and has a molecular weight of 2,000 to 1,500,000. Also disclosed is another acetaminophen formulation containing polyvinylpyrrolidone as high as 25-50% by weight.

25 Claims, No Drawings

POLYVINYLPYRROLIDONE-CONTAINING ACETAMINOPHEN LIQUID FORMULATIONS

BACKGROUND

Acetaminophen is an over-the-counter drug commonly used to relieve headaches and reduce fever.

A highly concentrated solution of acetaminophen allows a high dose of acetaminophen (e.g., 325 mg) to be formulated in a compact oral dosage form for easy swallowing. It also enhances the bioavailability of acetaminophen. However, acetaminophen tends to degrade or recrystallize in such a solution.

There is a need to develop an acetaminophen liquid formulation in a highly concentrated solution suitable for a compact dosage form.

SUMMARY

This invention is based on an unexpected discovery of a way to enhance the solubility of acetaminophen in a liquid formulation.

Accordingly, one aspect of this invention relates to a pharmaceutical formulation containing acetaminophen as the only active ingredient and a solvent system for dissolving the acetaminophen. The acetaminophen is 10-60% (e.g., 15-40% or 20-35%) by weight of the formulation. The solvent system, in addition to water and polyethylene glycol, further includes polyvinylpyrrolidone that is 2-50% (e.g., 5-30% or 10-25%) by weight, also of the formulation, and has a molecular weight of 2,000 to 1,500,000 (e.g., 2,000 to 62,000, 2,000 to 4,000, or 4,000 to 18,000). Note that the formulation is free of any ionizing agent; namely, a compound capable of ionizing an active ingredient, acetaminophen here, in a solution.

The above-described pharmaceutical formulation can further contain propylene glycol in its solvent system.

Another aspect of this invention relates to a similar acetaminophen formulation that is not necessarily free of another active ingredient or free of an ionizing agent. Again, the acetaminophen is 10-60% (e.g., 15-40% or 20-35%) by weight. Likely, the solvent system, in addition to water and polyethylene glycol, further includes polyvinylpyrrolidone and, optionally, propylene glycol. The polyvinylpyrrolidone has a molecular weight of 2,000 to 1,500,000 (e.g., 2,000 to 62,000, 2,000 to 4,000, or 4,000 to 18,000). Its content in this formulation is 25-50% (e.g., 25 to 35%) by weight.

Also within the scope of this invention is the use of the above-described pharmaceutical formulations for the manufacture of medicaments that alleviate pain or reduce fever.

The details of one or more embodiments of the invention are set forth in the accompanying description below. Other features, objects, and advantages of the invention will be apparent from the description and the claims.

DETAILED DESCRIPTION

This invention provides a liquid pharmaceutical formulation that contains acetaminophen at a high concentration. The formulation is suitable for preparing various oral dosage forms, e.g., soft gel capsule, suspension, solution, syrup, two-piece hard shell capsule, and nasal/oral spray. See Modern Pharmaceutics, Volume 121(2004), edited by Gilbert S. Banker and Christopher T. Rhodes, and references cited therein. In particular, it may be used to prepare soft gels containing a high dose of acetaminophen in a stable solution, e.g., 250 mg or 325 mg acetaminophen per soft gel.

The pharmaceutical formulation of this invention contains acetaminophen and a solvent system for dissolving the acetaminophen.

The acetaminophen can be the only active ingredient in the formulation. The formulation can further contain one or more other active ingredients that can be co-dissolved with acetaminophen in the solvent system of this invention.

The acetaminophen can be either in its free form or in any pharmaceutically acceptable salt form.

The acetaminophen can be dissolved in the solvent system at an unexpectedly high concentration, e.g., 10-60%, 15-40%, or 20-35% by weight.

The solvent system in this invention contains polyvinylpyrrolidone, polyethylene glycol, and water. Optionally, it also includes other solvents such as propylene glycol, polysorbate 80 (i.e., Tween 80), and sugar alcohol (e.g., glycerol and sorbitol).

Polyvinylpyrrolidone, also known as Polyvidone or Povidone, is a water-soluble polymer. Polyvinylpyrrolidone used in this invention has an molecular weight in the range of 2,000 to 1,500,000, e.g., 2,000 to 62,000, 2,000 to 4,000, 4,000 to 18,000, or 6,000 to 15,000.

Polyvinylpyrrolidone products are commonly graded by K values. The K value is an index for correlating relative viscosity with the average degree of polymerization. See Cellulose Chem. 1932, 13, 60. The K value is calculated by the following formula:

$$K=(1.5 \log \eta_{rel}-1)/(0.15+0.003c)+(300c \log \eta_{rel}+(c+1.5c\log \eta_{rel})^2)^{1/2}/(0.15c+0.003c^2)$$

$\eta_{rel}$: Relative viscosity of aqueous polyvinylpyrrolidone solution to water. c: Content of polyvinylpyrrolidone in an aqueous polyvinylpyrrolidone solution (w/w%).

Polyvinylpyrrolidone used in the formulation has a K value of 12 to 90, e.g., 12, 15, 17, 25, or 30. Polyvinylpyrrolidone is designated as Povidone in the United States Pharmacopeial Convention ("USP"). Polyvinylpyrrolidone products are commercially available and generally include K values in their trade names, e.g., Polyvinylpyrrolidone K17 or Povidone K17.

There are correlations between K values and molecular weights. For example, polyvinylpyrrolidone K12 has a molecular weight of 2,000 to 4,000, K15 6,000 to 15,000, K17 4,000 to 18,000, K30 40,000 to 62,000, and K90 1,000,000 to 1,500,000. Polyvinylpyrrolidone products from different vendors may have different average molecular weights, which typically fall into the ranges cited above.

Polyvinylpyrrolidone herein refers to a single product or a mixture of several products. For example, it can be polyvinylpyrrolidone K12, K15, K17, K25, K30, K60, K90, or a mixture thereof. The amount of polyvinylpyrrolidone is 2-50%, 5-30%, or 10-25% by weight of the formulation.

Polyvinylpyrrolidone enhances, in unexpected manners, the solubility of acetaminophen in the solvent system containing polyvinylpyrrolidone, polyethylene glycol, water, and optionally propylene glycol or other components.

Polyethylene glycol, also known as "PEG," has a formula of $H(OCH_2CH_2)_nOH$, wherein n is 4 or greater. A number generally follows the name PEG to indicate its average molecular weight. For example, PEG-400 has an average molecular weight of about 400. See Cosmetic Ingredient Dictionary, 3d Ed. (1982), pages 201-03; Merck Index, 10th Ed. (1983), page 1092.

Polyethylene glycol used in this invention is a clear viscous liquid or a white solid at room temperature, and can be dissolved in water and many organic solvents. Its molecular weight can be between 200 and 800, preferably 400. The solvent system may contain a single polyethylene glycol product or a mixture of two or more polyethylene glycol products.

Propylene glycol, a clear viscous liquid, has the formula $HOCH_2CHOHCH_3$. It is miscible with water and can be optionally included in the solvent system described above.

The term "ionizing agent" herein refers to a compound that can react with acetaminophen in the solvent system to form acetaminophen ions. Examples of an ionizing agent include both organic and inorganic bases capable of accepting hydrogen ions or donating electron pairs. Alkali or alkaline-earth metal salts or hydroxides are commonly used ionizing agents to increase the solubility of acetaminophen.

An ionizing agent can be added to the formulation to boost the solubility of acetaminophen in the solvent system. However, it can undesirably accelerate the degradation of acetaminophen. Thus, an acetaminophen formulation having an ionizing agent might be less stable. Based on the required shelf life of a formulation, a person skilled in the art can easily decide whether or not to include an ionizing agent in the formulation. In the formulation of this invention that does not include an ionizing agent, acetaminophen is dissolved at an unexpectedly high concentration in the solvent system, which, as pointed out above, contains polyvinylpyrrolidone, polyethylene glycol, and water.

The term "dissolving" herein means "evenly dispersing acetaminophen as molecules in the solvent system containing polyvinylpyrrolidone, polyethylene glycol, and water for at least three days, as judged by the naked eye or by a magnifying optical device based on two criteria: (i) transparence of the solution, and (ii) no formation of solid precipitation."

The transitional phrase "consisting essentially of" or "consists essentially of" as used herein limits the scope of a claim to the specified materials or steps and those that do not materially affect the basic and novel characteristics of the claimed invention.

Unexpectedly, polyvinylpyrrolidone continues to enhance the solubility of acetaminophen when present in the above-described solvent system at ≥25% by weight, contrary to the belief that polyvinylpyrrolidone beyond 20% by weight ceases to further enhance the solubility of acetaminophen.

The formulations of this invention can further contain a preserving agent, a stabilizing agent, a wetting agent, a taste masking agent, or a coloring substance.

Below is a general procedure that can be used to prepare the formulation of this invention:

Polyethylene glycol (e.g., PEG-400), water, polyvinylpyrrolidone, and one or more optional solvents (e.g., propylene glycol) or other agents (e.g., sodium acetate) are mixed at an elevated temperature to form a clear solvent system. The acetaminophen is then dissolved in the solvent system. The resulting solution can further be processed, e.g., deaerated and sterilized. The dissolution of acetaminophen in the formulation can be determined visually based on both transparence of the solution and lack of solid precipitation. Further, the dissolved acetaminophen in the formulation can be assayed by analytical methods, such as thin layer chromatography and/or high performance liquid chromatography.

A person skilled in the art can determine without undue experimentation the order of adding polyvinylpyrrolidone, polyethylene glycol, water, and other components, if any, their relative amounts, and the mixing/dissolving temperatures to form the solvent system and to dissolve acetaminophen. Indeed, a skilled artisan can make adjustments of the above to obtain a desired concentration of acetaminophen in the system.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are incorporated by reference in their entirety.

EXAMPLE 1

Polyethylene glycol 400 (575 mg) and propylene glycol (54.5 mg) were mixed with stirring at 250-350 rpm. The mixture was slowly heated to 170±5+ F. Subsequently, polyvinylpyrrolidone K17 (115.0 mg) was added to the mixture at the same temperature. After the mixture turned into a clear solution with constant stirring, water (80.5 mg) and acetaminophen (325 mg) were then added. The acetaminophen-containing solution was further stirred at 170±5° F. for 45 minutes until it became clear. The clear acetaminophen solution was then removed from the heat source and deaerated in a vacuum desiccator (a vacuum between 26 to 30 inches of mercury) at room temperature for 20-30 minutes. The solution, containing acetaminophen in an amount as high as 28.3% by weight, was visually evaluated. Unexpectedly, it remained clear for 3 days (indeed, for more than eight months) despite the high acetaminophen concentration.

EXAMPLE 2

Polyethylene glycol 400 (575 mg) and propylene glycol (54.5 mg) were mixed with stirring at 250-350 rpm. The mixture was slowly heated to 170±5° F. Subsequently, polyvinylpyrrolidone K30 (115.0 mg) was added to the mixture at the same temperature. After the mixture turned into a clear solution with constant stirring, water (80.5 mg) and acetaminophen (325 mg) were then added. The acetaminophen-containing solution was further stirred at 170±5° F. for 45 minutes until it became clear. The clear acetaminophen solution was then removed from the heat source and deaerated in a vacuum desiccator (a vacuum between 26 to 30 inches of mercury) at room temperature for 20-30 minutes. The solution, containing acetaminophen in an amount as high as 28.3% by weight, was visually evaluated. Unexpectedly, it remained clear for 3 days despite the high acetaminophen concentration.

EXAMPLE 3

Polyethylene glycol 400 (575 mg) and propylene glycol (54.5 mg) were mixed with stirring at 250-350 rpm. The mixture was slowly heated to 170±5° F. Subsequently, polyvinylpyrrolidone K12 (230.0 mg) was added to the mixture at the same temperature. After the mixture turned into a clear solution with constant stirring, water (80.5 mg) and acetaminophen (325 mg) were then added. The acetaminophen-containing solution was further stirred at 170±5° F. for 45 minutes until it became clear. The clear acetaminophen solution was then removed from the heat source and deaerated in a vacuum desiccator (a vacuum between 26 to 30 inches of mercury) at room temperature for 20-30 minutes. The solution, containing acetaminophen in an amount as high as 25.7% by weight, was visually evaluated. Unexpectedly, it remained clear for 3 days despite the high acetaminophen concentration.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A liquid pharmaceutical formulation consisting essentially of acetaminophen as the only active ingredient and a solvent system for dissolving the acetaminophen, wherein the acetaminophen is 10-60% by weight of the formulation, the solvent system consists essentially of water, polyethylene glycol, propylene glycol, and polyvinylpyrrolidone, the polyvinylpyrrolidone having a molecular weight of 2000 to 1,500,000 and being 2-50% by weight of the formulation, and the formulation is free of any ionizing agent, wherein the formulation remains clear for at least 3 days at room temperature and the water is about 6.36-7.00% by weight of the formulation.

2. The liquid pharmaceutical formulation of claim 1, wherein the acetaminophen is 15-40% by weight of the formulation, and the polyvinylpyrrolidone, has a molecular weight of 2,000 to 62,000 and is 5-30% by weight of the formulation.

3. The liquid pharmaceutical formulation of claim 1, wherein the polyvinylpyrrolidone has a molecular weight of 2,000 to 4,000.

4. The pharmaceutical formulation of claim 2, wherein the acetaminophen is 20-35% by weight of the formulation and the polyvinylpyrrolidone is 10-25% by weight of the formulation.

5. The pharmaceutical formulation of claim 2, wherein the polyvinylpyrrolidone has a molecular weight of 2,000 to 4,000.

6. The pharmaceutical formulation of claim 5, wherein the acetaminophen is 20-35% by weight and the polyvinylpyrrolidone is 10-25% by weight of the formulation.

7. The pharmaceutical formulation of claim 2, wherein the polyvinylpyrrolidone has a molecular weight of 4,000 to 18,000.

8. The pharmaceutical formulation of claim 6, wherein the acetaminophen is 20-35% by weight of the formulation and the polyvinylpyrrolidone is 10-25% by weight of the formulation.

9. The pharmaceutical formulation of claim 2, wherein the polyvinylpyrrolidone has a molecular weight of 6,000 to 15,000.

10. The pharmaceutical formulation of claim 9, wherein the acetaminophen is 20-35% by weight of the formulation and the polyvinylpyrrolidone is 10-25% by weight of the formulation.

11. The pharmaceutical formulation of claim 2, wherein the polyethylene glycol has a molecular weight of 200-800.

12. The pharmaceutical formulation of claim 11, wherein the polyvinylpyrrolidone has a molecular weight of 2,000 to 4,000.

13. The pharmaceutical formulation of claim 12, wherein the acetaminophen is 20-35% by weight of the formulation and the polyvinylpyrrolidone is 10-25% by weight of the formulation.

14. The pharmaceutical formulation of claim 11, wherein the polyvinylpyrrolidone has a molecular weight of 4,000 to 18,000.

15. The pharmaceutical formulation of claim 14, wherein the acetaminophen is 20-35% by weight of the formulation and the polyvinylpyrrolidone is 10-25% by weight of the formulation.

16. The pharmaceutical formulation of claim 11, wherein the polyvinylpyrrolidone has a molecular weight of 6,000 to 15,000.

17. The pharmaceutical formulation of claim 16, wherein the acetaminophen is 20-35% by weight of the formulation and the polyvinylpyrrolidone is 10-25% by weight of the formulation.

18. The pharmaceutical formulation of claim 3, wherein the acetaminophen is 15-40% by weight of the formulation and the polyvinylpyrrolidone is 5-30% by weight of the formulation.

19. The pharmaceutical formulation of claim 3, wherein the acetaminophen is 20-35% by weight of the formulation and the polyvinylpyrrolidone is 10-25% by weight of the formulation.

20. The pharmaceutical formulation of claim 3, wherein the polyethylene glycol has a molecular weight of 200-800.

21. The pharmaceutical formulation of claim 20, wherein the acetaminophen is 15-40% by weight of the formulation and the polyvinylpyrrolidone is 5-30% by weight of the formulation.

22. The pharmaceutical formulation of claim 20, wherein the acetaminophen is 20-35% by weight of the formulation and the polyvinylpyrrolidone is 10-25% by weight of the formulation.

23. The pharmaceutical formulation of claim 1, wherein the polyethylene glycol has a molecular weight of 400.

24. A method of preparing a liquid pharmaceutical formulation of claim 1, which method comprises:
  (a) stirring polyethylene glycol and propylene glycol to obtain a mixture, the polyethylene glycol having an average molecular weight of 200-800;
  (b) heating the mixture to a temperature of 170±5° F. with stirring to obtain a heated mixture;
  (c) adding polyvinylpyrrolidone to the heated mixture with stirring at the same temperature to obtain a clear solution;
  (d) adding purified water to the clear solution with stirring at the same temperature to obtain an aqueous solution;
  (e) adding acetaminophen to the aqueous solution with stirring at the same temperature to obtain an acetaminophen solution;
  (f) stirring the acetaminophen solution at the same temperature to obtain a clear acetaminophen solution, and
  (g) cooling to ambient temperature and deaerating the clear acetaminophen solution.

25. The pharmaceutical formulation of claim 1, wherein the water is about 6.36% or 7.00% by weight of the formulation.

* * * * *